(12) United States Patent
Harvie (10) Patent No.: US 9,788,992 B2
(45) Date of Patent: Oct. 17, 2017

(54) HYDRO-BLOCK AIR VENT CONDOM CATHETER AND METHOD OF USE

(71) Applicant: Mark R. Harvie, Williston, VT (US)

(72) Inventor: Mark R. Harvie, Williston, VT (US)

( * ) Notice: Subject to any disclaimer, the term of this patent is extended or adjusted under 35 U.S.C. 154(b) by 835 days.

(21) Appl. No.: 14/270,467

(22) Filed: May 6, 2014

(65) Prior Publication Data

US 2015/0320583 A1    Nov. 12, 2015

(51) Int. Cl.
| | |
|---|---|
| A61F 5/453 | (2006.01) |
| A61F 5/441 | (2006.01) |
| A61F 5/455 | (2006.01) |
| A61M 1/00 | (2006.01) |
| A61M 25/00 | (2006.01) |

(52) U.S. Cl.
CPC .............. *A61F 5/441* (2013.01); *A61F 5/453* (2013.01); *A61F 5/455* (2013.01); *A61M 1/0066* (2013.01); *A61M 25/0017* (2013.01); *A61M 2205/3379* (2013.01)

(58) Field of Classification Search
CPC ................................. A61F 5/441; A61F 5/453
USPC .......................................... 604/347, 349–353
See application file for complete search history.

(56) References Cited

U.S. PATENT DOCUMENTS

| | | | | |
|---|---|---|---|---|
| 3,661,143 A | * | 5/1972 | Henkin | A61M 1/0019 600/575 |
| 4,656,675 A | * | 4/1987 | Fajnsztajn | A61F 5/441 4/144.3 |
| 5,002,541 A | * | 3/1991 | Conkling | A61F 5/44 604/319 |
| 5,346,483 A | * | 9/1994 | Thaxton, Sr. | A61F 5/453 600/580 |
| 6,248,096 B1 | * | 6/2001 | Dwork | A61F 5/453 604/347 |
| 7,018,367 B2 | * | 3/2006 | Nava | A61F 5/453 4/144.3 |
| 2002/0087130 A1 | * | 7/2002 | Guldfeldt | A61F 5/453 604/317 |
| 2012/0029452 A1 | * | 2/2012 | Rodsten | A61F 5/4408 604/353 |
| 2012/0245541 A1 | * | 9/2012 | Suzuki | A61F 5/441 604/319 |

* cited by examiner

*Primary Examiner* — Susan Su (74) *Attorney, Agent, or Firm* — Eric R. Benson (57) ABSTRACT

This invention is a device that utilizes hydro-block venting material in various condom catheter configurations to permit adequate airflow into the catheter thereby permitting efficient and complete drainage of urine away from the user following urination by means od gravity, siphoning or pumping. In one embodiment the condom that fits on the penis is itself made of hydro-block venting material. In another embodiment the hydro-block material is placed on the proximal end of a storage bag. In yet another embodiment a retro-fit assembly containing the hydro-block venting material can be retrofitted for use with any condom catheter. Both adhesive and inflatable rings are disclosed as attachment means to secure the condom catheter to the user and prevent leakage.

8 Claims, 5 Drawing Sheets

HYDRO-BLOCK AIR VENT CONDOM CATHETER AND METHOD OF USE

BACKGROUND ART

The use of condoms in ancient civilizations is a subject of much debate among archaeologists and historians. The oldest claimed representation of condom use is a 12,000 to15,000 year old painting in the French cave known as Grotte des Combarrelles. The Ancient civilizations of Rome, Greece, and Egypt typically had small families by the practice of a variety of birth control methods. Despite the fact that these societies at that time viewed birth control as a woman's responsibility there are references to male-controlled contraceptive methods, i.e. condoms, etc.

References in historical documents to condoms exist but are generally difficult to find. A major contributing factor to the loss of any significant contraceptive historical documentation was the rise of Catholicism which considers all forms of birth control to be a sin. Various Jewish and Muslim writings from the Middle Ages refer to attempts at other interesting if not imaginative male-controlled contraception, including such things as covering the penis in tar or soaking the penis in onion juice. It is well documented, however, that prior to the 15th century glans condoms (devices that cover only the head of the penis) were used as a means of birth control in Asia by members of the upper classes. The historical record indicates that glans condoms in China were typically made from oiled silk paper and/or lamb's intestines while the Japanese made them from tortoise shells or animal horns.

The first documented pandemic of syphilis began in Europe in 1494 and by 1505 had spread to China killing an unverifiable millions of people. It was during this pandemic that the use of a condom as a medical device, i.e disease barrier, first appears in the historical record. In 1564 Gabriele Falloppio authored *De Morbo Gallico* (referring to syphilis) wherein he recommended as a prevention of syphilis the use of a condom that he claimed to have invented. The Falloppio condom was comprised of linen sheaths soaked in a chemical solution and allowed to dry before use. The cloths were sized to cover the glans of the penis and were held on with a pink ribbon. The thought being that the pink ribbon would be more attractive for the ladies. Fallopio conducted what appears to be the first clinical trial of the efficacy of his condom device as a disease barrier on 1100 men and reported that "I call immortal God to witness that not one of them was infected." After the 1564 publication of *De Morbo Gallico* the use of condoms to protect from disease is described in a wide variety of historically significant documents throughout Europe.

On Jul. 3, 1981, the New York Times broke the story on a new public health threat, an acquired immunodeficiency syndrome (AIDS). It was not until 1982, however, that it was first suggested that the disease was sexually transmitted. It was in response to these findings that the U.S. Surgeon General Dr. C. Everett Koop publically supported condom promotion programs as a means of AIDS transmission prevention.

Condoms and condom-like devices eventually would be used to assist in the medical and hygiene care of male patients affected by urinary incontinence. Ancient reports on urinary incontinence are rather rare and mainly address cases of extraurethral incontinence (e.g. due to a fistula acquired during childbirth) or overflow incontinence (e.g. in males with urinary retention or after spinal cord injury). In later centuries several authors dealt with the problem of postoperative incontinence after perineal lithotomy. Defined surgical techniques for the cure of urinary incontinence, however, were not introduced before the $19^{th}$ century. First this was limited to fistula repair but by the end of the 19th century new procedures for stress incontinence were introduced and became standard clinical procedures. Other modern techniques, like artificial sphincters or electrostimulation, were alternatives developed in urology in the second half of the 20th century.

On the other hand the use of different catheters for the relief of urinary retention is described in many early cultures. Bloom D A, McGuire E J, Lapides J: *A brief history of urethral catheterization. J Urol* 1994; 151: 317-325. The first sources dealing briefly with urinary incontinence are Egyptian manuscripts from the $2^{nd}$ millennium B.C. the "*Papyrus Smith*" and the "*Papyrus Ebers*". Greek medicine was dominated by the outstanding work of Hippocrates (460-377 B.C.) who was writing extensively about the diseases of the urinary tract. Despite his discussion on perineal lithotomy Hippocrates also dealt extensively with urinary incontinence management.

The most famous surgeon of the Renaissance era, Ambroise Paré (1510-1590), had a great interest in the urinary tract and was one of the first surgeons to resect "carnosities" of the urethra. Paré described the alterations caused by subvesical obstruction and realized the mechanism of synchronized sphincter relaxation and detrusor contraction during micturition. Paré promoted the use of a portable urinal for incontinent males and an instrument that facilitates urination in the standing position after loss of the penis that looks remarkably similar to a modern condom catheter. In describing the use of this condom like device Paré is quoted as stating that "[t]hose that have their yards cut off close to their bellies, are greatly troubled in making urine, so that they are constrained to sit downe like women, for their ease. I have devised this pipe or conduit . . . that must be applied to the lower part of the os pectinis . . . serving instead of the yard in making of water, which therefore we may call an artificiall yard."

Urinals designed to be worn and into which the male penis would partially extend have been known for centuries. For example Wilhelm Fabricius Hildanus (1560-1634) provided a modified urinal for the treatment of incontinence in his work "De ardore et incontinentia urinae, et nova inventione instrumenti, quo inter deambulandum colligitur" consisting either of a glass container or the bladder of a pig that was attached to the body by straps. U.S. Pat. No. 480,911 reveals that a worn urinal into which the penis is inserted for penile discharges have been known in the patent art in the United States at least from 1892.

In his book "*Chirurgie*" the German Lorenz Heister (1683-1758) dedicated two chapters on male and female incontinence: "Wenn Manns-und Frauens-Personen den Urin nicht halten können". Besides the use of a urinal as described by Paré or Fabricius Hildanus, Heister suggested a penile clamp that was covered with leather and removed by the patient at the time of micturition. With reference to a colleague named Winslow, Heister designed a belt that produces perineal compression to the bulbar urethra.

The oldest device for external compression of the male urethra is the penile clamp. It was brought into use again by J. H. Cunningham as a helpful instrument for performing retrograde urethrography, a radiographic method that was introduced by him into urology in 1910, and is still named after Cunningham today. The first artificial sphincter that was designed as an inflatable circular cuff and applied to the male urethra by surgical means was created by Frederic E.

B. Foley (1891-1966) from St. Paul, Minn. and published in 1947. This ingenious urologist is best known for the improvement of the principles of the transurethral balloon catheter and played a major role in the introduction of commercially manufactured balloon catheters in the 1930's.

The prior art is replete with examples of male urinary incontinence devices claiming to provide a satisfactory device for wear by men. Such a device should be: easily applied; comfortable; leak proof; remain securely attached over a considerable period of time without discomfort regardless of the activity level of the user; accommodating of a sudden surge flow of urine; hygienic; cost effective to manufacture; and be removable without pain or discomfort. The prior art devices fulfill some of these essentials but otherwise each are totally inadequate on others.

The use of external catheters, i.e. the condom or Texas catheter for treating male urinary incontinence is well known, as disclosed in U.S. Pat. Nos. 4,378,018, 4,187,851, 3,863,638, 3,835,857 and 4,475,910. These external urinary drainage means or condom catheters first appear in the patent literature in German Pat. No. 520.401. These condom catheters are typically comprised of an elastic sheath adapted to fit over the penis. The sheath is manufactured with an outlet at its distal end that can be connected to a tube or other collection means. The sheath is typically designed with a constricted downstream end portion adapted for fluid-tight connection with a drain tube. The sheath is usually comprised of a thin elastomeric fluid-impermeable material such as latex rubber or silicone rubber. This sheath is for all intents and purposes similar to a condom which can be rolled onto the penis.

The prior art teaches several attachment means for condom catheters to the penis which include non adhesive and adhesive catheters. Non-adhesive condom catheters are held in place with either an inflatable ring such as the Cook Non-Adhesive Silicone Condom Catheter or a Velcro strap that can be wrapped around the sheath. These types of condom catheters are typically reusable.

The most popular condom catheter in use today are the one piece self-adhesive condom catheters. These condom catheters are easier to put on by rolling it over the shaft of the penis and then by pressing the catheter against the skin to help the adhesive to stick to the penis. Recent condom catheters are typically made entirely of silicone since it has been reported that these types of condom catheters are less likely to cause skin irritation or cause other adverse reactions. These of course are a good alternative for those in men with a latex allergy or sensitivity. A variation of these types of one piece condom catheters is the current art AlphaDry condom catheter which consists of a one way valve and a small reservoir that can be stored in a user's underwear.

Also available in the current art are two piece condom catheters which consist of a sheath and separate hydrocolloid strips. These hydrocolloid strips have adhesive surfaces on both the inside and outside. The hydrocolloid strips are first wrapped around the penis. The condom catheter is then rolled up the penis toward the abdomen over the strips and once unrolled it is then pressed to stick against the hydrocolloid strips that is adhered to the penis. A significant problem exists with this type of condom catheter because many users apparently will put on the strips in a way that is too tight for the penis causing irritation, restriction of blood flow and in some extreme cases, necrosis.

The Liberty Pouch™ is a small external flower shaped wafer that is applied and sealed to the penis tip. The Liberty Pouch™ is made of a hydrocolloid material and covered by a second layer of material that wraps around the glans or head of the penis for protection. The outside of the Liberty Pouch™ is designed to direct expelled urine into a tube for collection in a bag typically stored in the underwear or pants of a user. The Liberty Pouch™ is beneficial for men with either a short or retracted penis and also for un-circumcised men. The foreskin of the un-circumcised penis is retracted to allow application of the device and then brought forward to cover it. There are a large variety of external pouch types of condom catheters available. Because these pouch type condom catheters typically are adhered directly to the skin a user needs to remove the pubic hair surrounding the base of the penis often resulting in skin irritation.

It is well known in the art that using external condom catheters can cause a variety of serious problems for the user. These problems include skin irritation, maceration of the penis tip, urinary tract infections (UTI), ischemia and penile edema or urethral obstruction. Many of these complications occur frequently when the catheter: is not put on correctly; is used for longer than recommended; causes skin to be constantly wet which often softens the skin which eventually will be worn away by the condom catheter. Skin barrier products are often used prior to the application of the condom catheter to protect the skin from constant wetness but these have proven to be ineffective in preventing these potentially life threatening conditions.

The use of adhesive straps, especially with the condom catheters with adhesive on both sides, is known to cause strangulation of the penis or to excessively constrict it. Condom catheters are also known to cause infections which typically stems from the fact that all current art condom catheters are ineffective in preventing urine from accumulating and remaining against the penis and often times the urethra. Current art condom catheters are designed to prevent leakage of urine but at the same time they also prevent air from reaching the skin which would permit the urine to drain and prevent anaerobiosis of urinary tract infectious agents. The skin of a user can also break down with minor erosion and dermatitis resulting from lack of air and presence of urine.

It has been suggested that clear silicone condom catheters allow a user to see their skin condition while they are worn and also allow some oxygen and water vapor to reach the skin. This is largely anecdotal and would depend upon the fit of the condom catheter. Even with more rigid clear silicone condom catheters the buildup of urine occurs especially if the condom catheter fits more snuggly on the penis.

Backflow leakage is a persistent problem in condom catheters as well resulting from fluid backflow between the penis and the sheath of the condom. In an attempt to resolve this problem the prior art teaches the interposing of a sealant pad between the sheath and the penis as disclosed in U.S. Pat. Nos. 4,187,851 and 4,378,018. The consequences of the backflow of urine are well known, urinary tract infections, sores, discomfort and other related problems. Sealant pads are designed to prevent leakage and to retain the catheter in place. It is well known in the art that there are significant problems with this design in fitting these pads and catheters on the penis exactly as intended. The pad depicted in U.S. Pat. No. 4,187,851 for example is comprised of an adhesive strip intended to be wrapped around the penis before the condom catheter is unrolled into position. This process is difficult if not impossible for most patients suffering from urinary incontinence since they often lack the ability to undertake such intricate maneuvers. Attending medical personnel are often unable or unwilling to take the time necessary for properly wrapping and molding the sealant pads in place, and then carefully fitting the sheaths over the pads to form the necessary leak proof seal. Additionally the problems that may result from the improper application of such a condom catheter often are more serious than backflow leakage or patient discomfort, i.e. urinary tract infections and sores. In the event an adhesive pad as shown in U.S. Pat. No. 4,187,851 is wrapped too tightly around the penis, circulation might be impaired and tissue necrosis could result.

Condom catheters are also available with an internal coating of pressure sensitive adhesive eliminating the need for using a separate adhesive-coated sealant pads, as depicted in U.S. Pat. No. 4,475,910. This composition does appear to avoid some of the serious dangers that have been associated with the wrap around sealant pads described above, however, the known difficulties of applying these types of condom catheters coupled with the problem of leakage resulting from improper application persist and they may even be worse. Inordinate care is necessary when unrolling these types of adhesive coated condom catheters over the penis to make certain that the condom catheter is evenly applied without wrinkles or flow channels. Making matters worse many users while trying to handle these condom catheters frequently experience the adhesive coated inner surface coming into contact with each other and sticking together during application of the catheter. Separation of these surfaces after they have stuck together is virtually impossible. The result often prevents any corrective steps being taken and leakage of the condom catheter is for all intents and purposes a certainty.

U.S. Pat. No. 4,589,874 teaches the use of a condom catheter that has an inner sleeve designed to be stretched about the glans of the penis to prevent backflow and protect the delicate skin from injury that may be caused by longterm contact with residual urine that may remain near the outlet end of the sheath when the catheter is used. Whether these catheters are held in place by adhesive coating or an adhesive pad, they all require for proper placement of the inner sleeve into a fluid-tight contact with the glans portion of the penis before the proximal portion of the condom catheter may be adhesively secured to the penis. Again, this is a major difficulty in the use of these types of condom catheters and consequently are particularly unpopular.

Attempts have been made as shown in the prior art to try and resolve the backwash effect by introducing various means of removing accumulated urine by various means such as wicking fibers. For instance U.S. Pat. No. 4,820,289 discloses a condom catheter flocked with particles of fiber. This disclosed flocked external condom catheter is comprised of a sheath adapted to fit over the penis with a constricted downstream end portion adapted for a fluid-tight connection with a drain tube. One of the surfaces disclosed in this patent is comprised of a thin layer of adhesive and a uniform layer of small particles of a bonded fabric.

Other prior art patents of generally relating to condom catheters are U.S. Pat. Nos. 4,022,213, 4,284,079, 3,405,714, 4,239,044, 3,353,538, 3,511,241, 3,721,243, 3,631,857, 3,788,324, 3,339,551, 3,364,932, 4,296,502, and 3,742,953.

The prior art condom catheters, while partially effective in aiding male suffering with incontinence, as disclosed above, each have a number of significant problems such as:

1) Attachment by adhesive which is difficult to obtain an effective seal without channeling issues occurring and causing a serious skin irritation and damage upon removal for many users;
2) Difficulty in applying and removing the condom catheter without injuring the penis;
3) Difficulty in securely attaching the condom catheter to a user such that it remains functional, despite activity and a flaccid condition of the penis; and
4) Accumulation of urine that causes irritation and urinary tract and other types of infections.

There are no prior art condom catheters that solve all of these problems. Therefore there is a great need for a condom catheter device that is easily donned and remains securely in place regardless of the activity level of the user. Furthermore, to solve the problems of the prior art devices this condom catheter must also effectively facilitate the aspiration of backwashed urine that may accumulate between the penis and the condom catheter that is unable to drain from the distal or discharge end of the condom catheter. My invention is designed to solve these problems that exist in the current art.

DISCLOSURE OF THE INVENTION

Purpose of Invention

The purpose of the invention is to provide a condom catheter that will permit air to enter into the device by means of a Hydro-block or similar substance air vent that allows air to flow into the condom catheter while blocking the urine from exiting except through the distal end drain as intended. This invention will allow the urine to completely drain out of the condom catheter and the hose and completely away from the user's skin.

Description of Problems Solved by Invention

There is currently no condom catheter devices that will fit a user securely enough to allow for reasonable physical activity of a user that will also permit air to enter into the condom and thereby allow any backwashed urine to escape, thereby preventing such adverse medical conditions as skin irritation, maceration of the penis tip, urinary tract infections (UTI), ischemia and penile edema or urethral obstruction. The current invention incorporates a proprietary Hydroblock air vent that allows air to flow into the condom catheter while blocking the urine from exiting except through the distal end intended drain. This invention will allow the urine to completely drain out of the condom catheter and any attached hose and ultimately away from the user's skin, unlike current art condom catheters which permit urine to accumulate and remain in contact with the user's skin and urethra. The use of the invention disclosed in these letters patent will result in significant reduction in skin ulcers, maceration and UTI, all of which are currently major problems of significant cost to an already over burdened healthcare system. The invention disclosed in these letters patent may also be used with pump drainage systems such as the Omni URINCare® when gravity is not adequate to drain the condom catheter, such as night time use and fully reclined and raised legs positions such as in hospital beds in a trendelenburg position.

Additionally the invention disclosed in these letters patent in the most preferred embodiment has a series of inflatable rings, which when inflated will hold the condom in place in a more effective manner than the current single inflatable ring Cook condom catheter. This is superior in both its capacity to stay on a user while simultaneously reducing the amount of pressure needed in the rings in order to stay on, which potentially can cause strangulation of the penis which is accomplished in this invention by increasing the holding contact surface area of the inflatable rings.

The inflatable ring embodiment of this invention is designed to avoid the need to use adhesives to hold the Condom catheter in place, thereby eliminating entirely the adverse effects of adhesive contact and resultant skin damage and pain associated therewith. The most critical function of the invention disclosed in these letters patent is the aeration of the condom catheter. Therefore it would be obvious to one skilled in the art to use an adhesive type of attachment means to hold my invention with the Hydro-block or similar substance air vent in place.

Brief Description of Invention

My invention is a condom catheter which incorporates a proprietary Hydro-block or similar substance air vent that allows air to flow into the condom catheter while blocking the urine from exiting except through the intended drainage site at the distal end of the condom catheter. This invention will allow the urine to completely drain out of the condom catheter and any attached hose and ultimately away from the user's skin. Additionally the invention disclosed in these letters patent in the most preferred embodiment has a series of inflatable rings, which when inflated will hold the condom in place more effectively than the current art condom catheters.

BEST MODES FOR CARRYING OUT THE INVENTION

Preferred Embodiments
With reference now to the drawings, and in particular to FIGS. 1-8 thereof, are depicted four embodiments of a new and novel condom catheter utilizing hydro-block technology.

Figure 1:
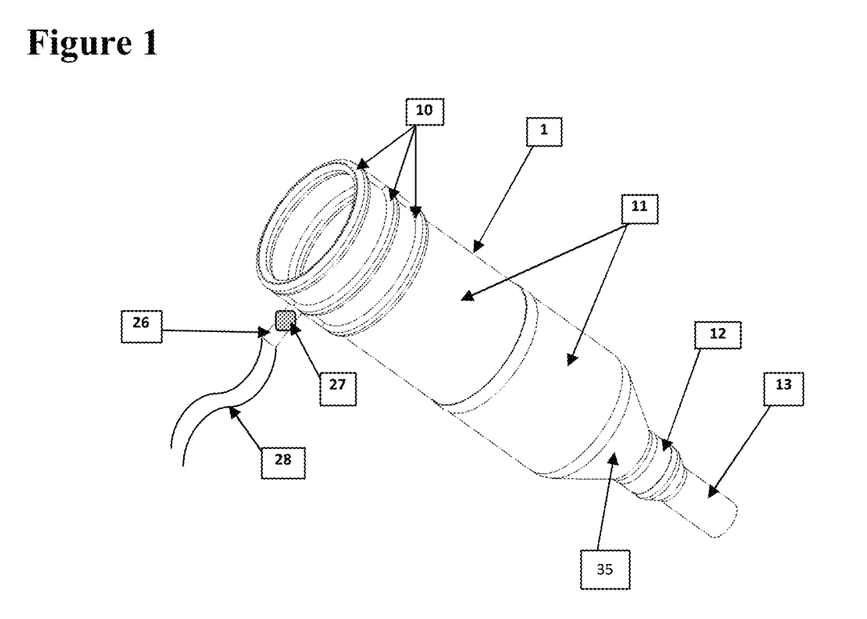
FIG. 1 is a proximal-side perspective view of the Hydro-Block Air Vent Condom Catheter with Inflatable Rings.

FIG. 1 depicts the Inflatable Ring embodiment of the Hydro-Block Air Vent Condom Catheter (1) which has a plurality of Inflatable Rings (10) disposed around the device to aid in maintaining the device securely sealed on a user's penis wherein the Hydro-Block Air Vent Condom Catheter (1) is comprised of Hydro-Block Air Vent (11).

Figure 2:
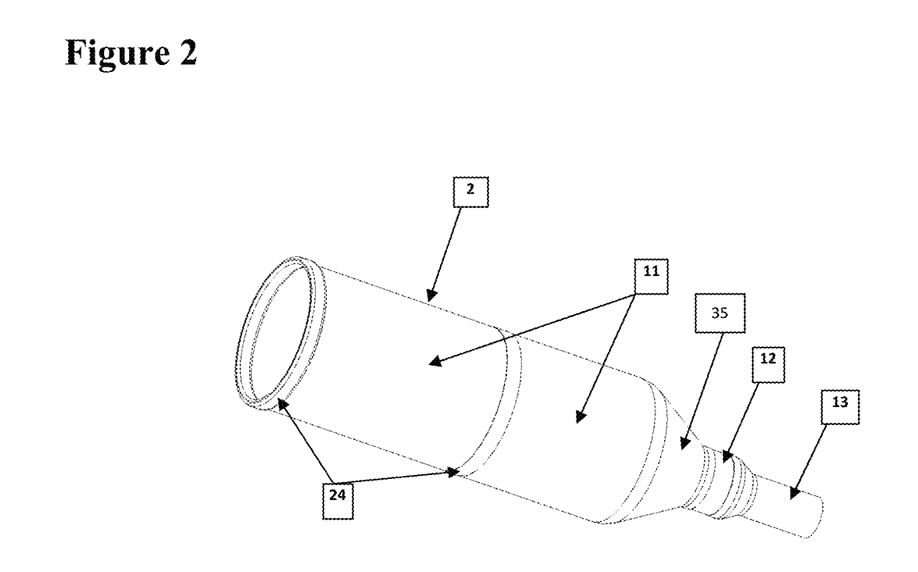
FIG. 2 is a proximal-side perspective view of the Hydro-Block Air Vent Condom Catheter without Inflatable Rings.

FIG. 2 depicts the Adhesive Ring embodiment of the Hydro-Block Air Vent Condom Catheter (2) which has a plurality of Adhesive Rings (24) disposed around the device to aid in maintaining the device securely sealed on a user's penis wherein the Hydro-Block Air Vent Condom Catheter (1) is comprised of Hydro-Block Air Vent (11).

Figure 3:
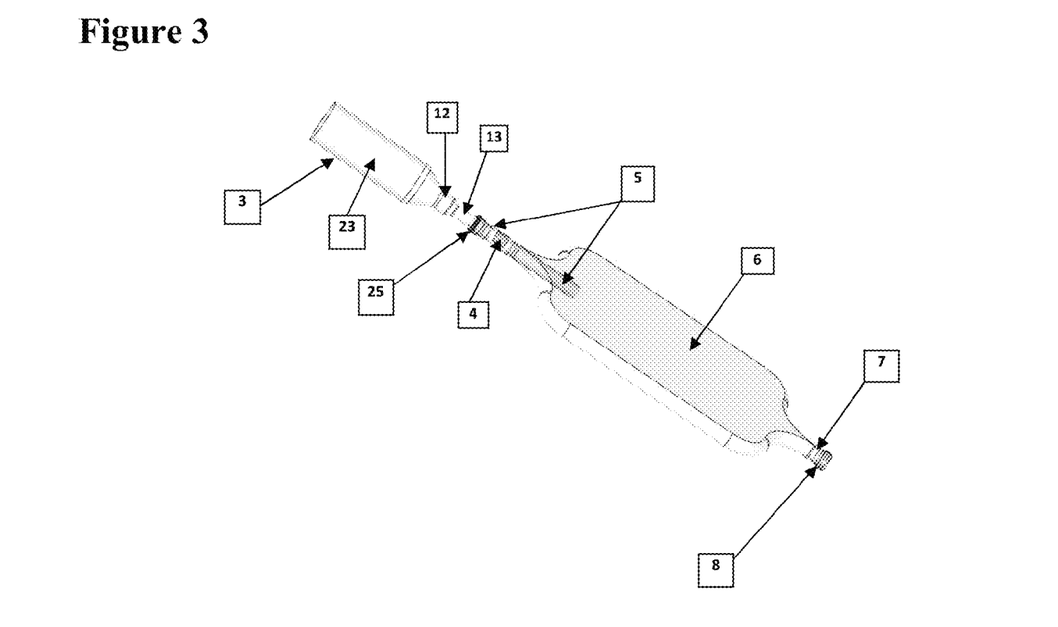
FIG. 3 is a proximal-side perspective view of the Hydro-Block Air Vent Condom Catheter without Inflatable Rings connected by a Hose to a Collections Bag.
Figure 4:
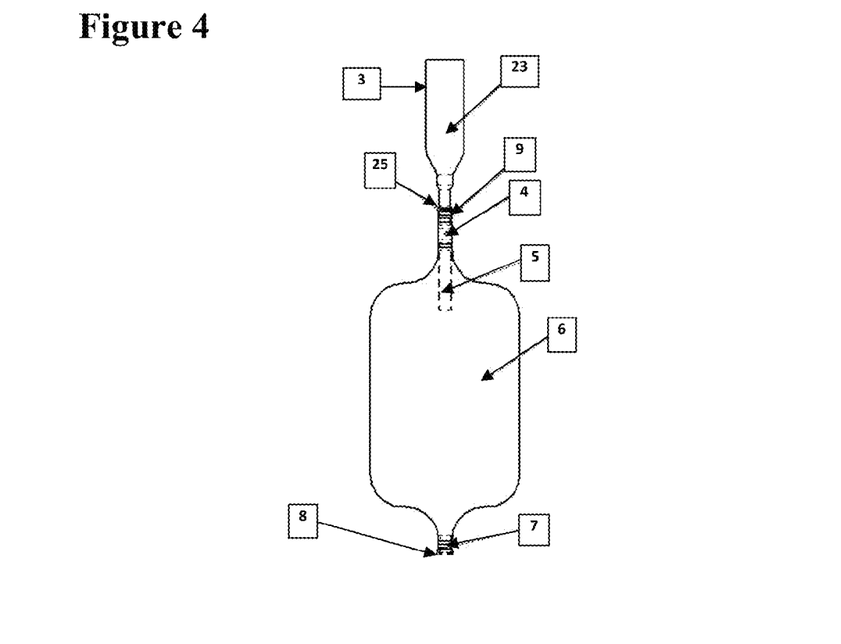
FIG. 4 is a front perspective view of the Hydro-Block Air Vent Condom Catheter without Inflatable Rings connected by a Hose to a Collections Bag.
Figure 5:
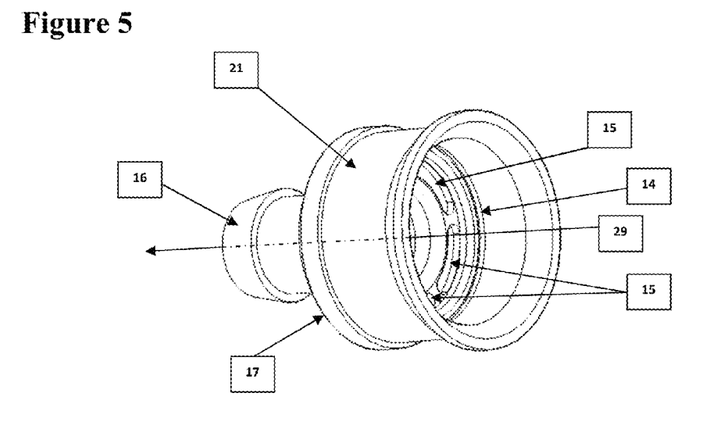
FIG. 5 is a proximal end perspective view of the Retro-Fit Assembly of the Retro-Fit Embodiment Hydro-Block Air Vent Condom Catheter.
Figure 6:
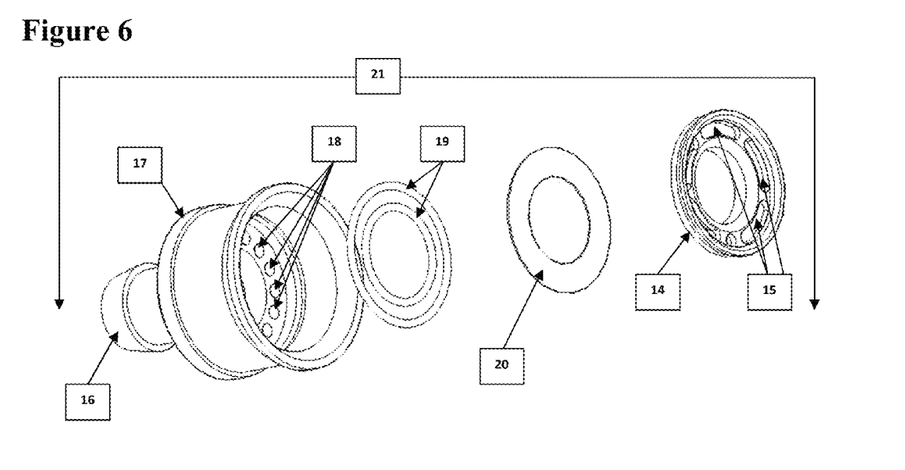
FIG. 6 is a proximal end exploded perspective view of the Retro-Fit Assembly of the Retro-Fit Embodiment Hydro-Block Air Vent Condom Catheter.

FIGS. 3 and 4 depict the Storage Bag Venting embodiment of the Hydro-Block Air Vent Condom Catheter (3) which vents air for proper drainage of the device by means of a Storage Bag Hydro-Block Air Vent (4) attached to the proximal end of a Storage Bag (6).

FIGS. 5, 6, 7 and 8 depict the Retro Fit Embodiment of the Hydro-Block Air Vent Condom Catheter (22) which utilizes a Retro-Fit Assembly (21) that may be used with any condom catheter on the market today.

Figure 7:
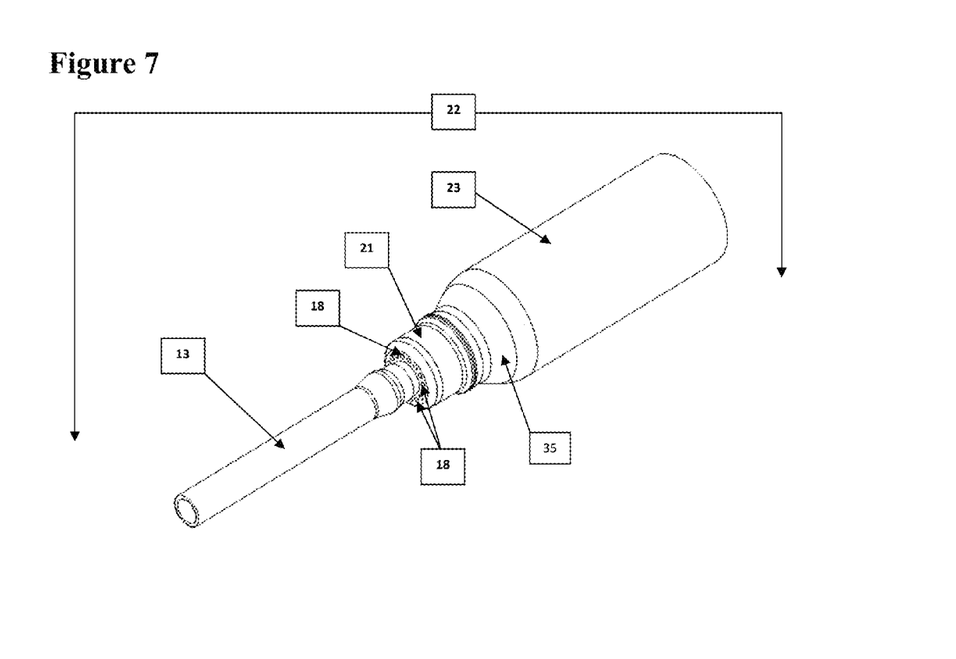
FIG. 7 is a distal end perspective view of the Retro-Fit Embodiment Hydro-Block Air Vent Condom Catheter.
Figure 8:
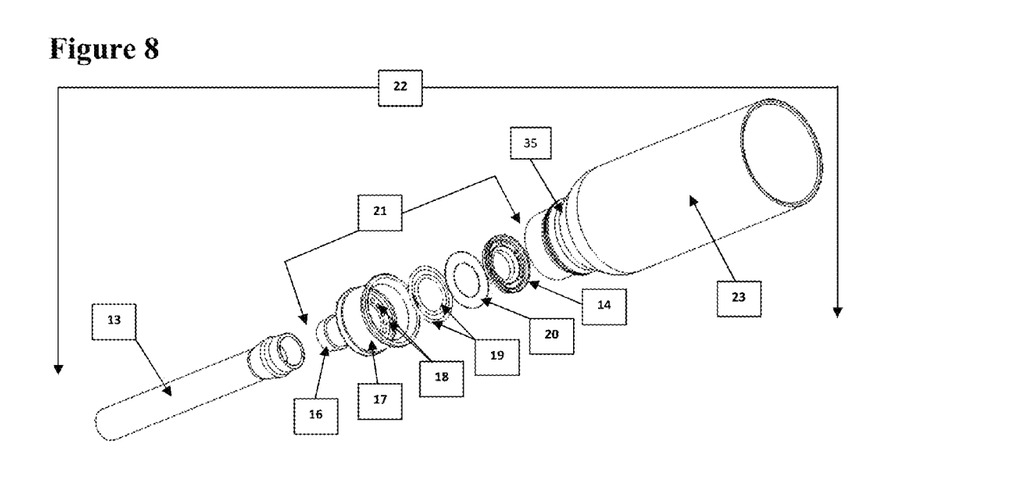
FIG. 8 is a proximal end exploded perspective view of the Retro-Fit Embodiment Hydro-Block Air Vent Condom Catheter.
Figure 9:
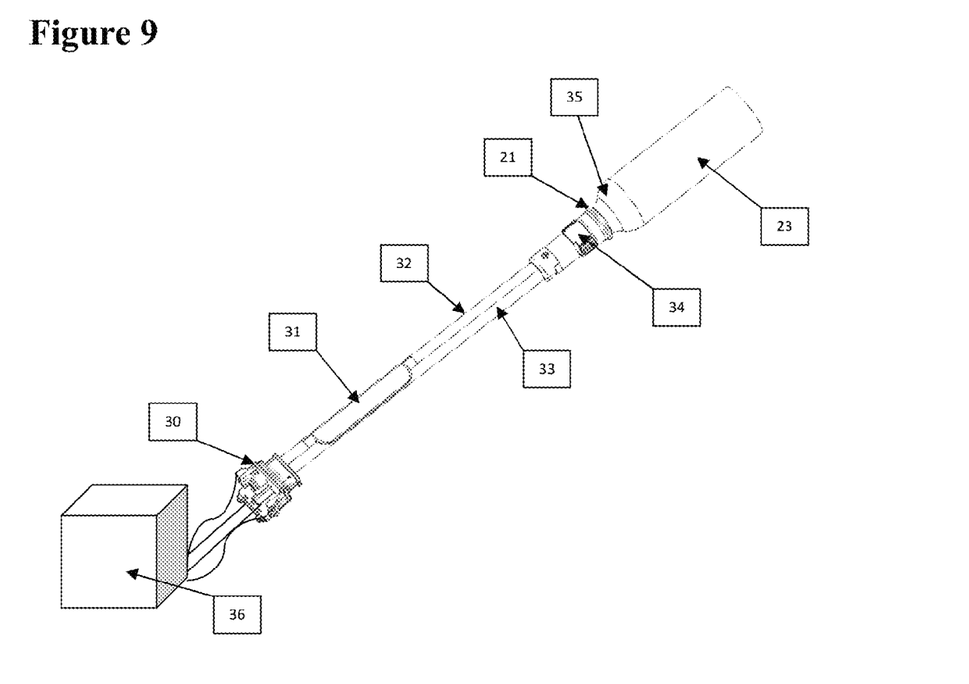
FIG. 9 is a proximal end perspective view of the assembled modified Retro-Fit Embodiment Hydro-Block Air Vent Condom Catheter configured with a quick disconnect hose system with pump connectivity and automatic urine sensing for pump activation.
Figure 10:
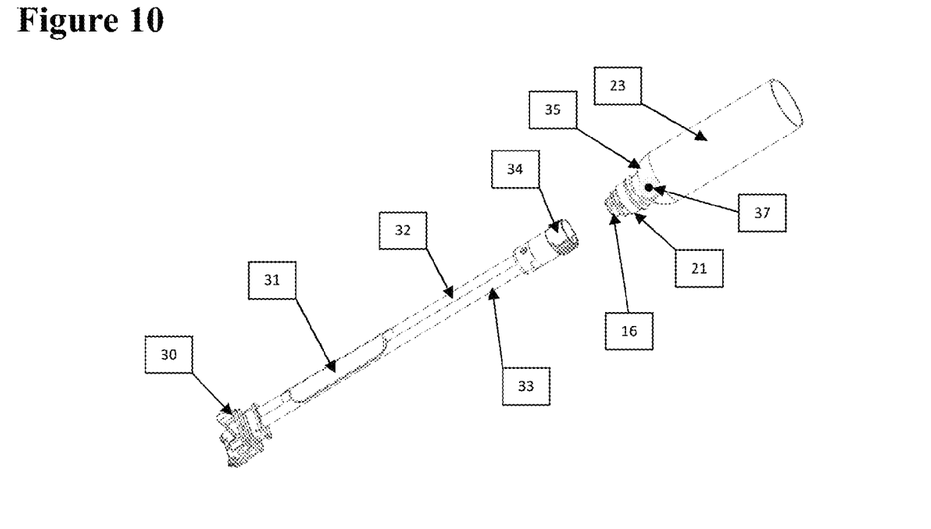
FIG. 10 is a proximal end exploded perspective view of the disassembled modified Retro-Fit Embodiment Hydro-Block Air Vent Condom Catheter configured with the quick disconnect hose system with pump connectivity and automatic urine sensing for pump activation disconnected from the condom portion of the device.

FIGS. 9 and 10 depict a modified Retro Fit Embodiment of the Hydro-Block Air Vent Condom Catheter (22) of FIGS. 7 and 8 wherein the Drain Tube (13) has been substituted with a quick disconnect system with pump connectivity and urine sensing to activate a pump comprised of a Pump and Sensor Connector (30), a Pressure Relief Balloon (31), a Liquid Hose (32), a Sensor Hose (33), and Quick Disconnect with Urine Sensor (34).

General Description of Reference Numerals in the Description and Drawings

Any actual dimensions listed are those of the preferred embodiment. Actual dimensions or exact hardware details and means may vary in a final product or most preferred embodiment and should be considered means for so as not to narrow the claims of the patent.

LIST AND DESCRIPTION OF COMPONENT PARTS OF THE INVENTION (1) Inflatable Ring embodiment of the Hydro-Block Air Vent Condom Catheter
(2) Adhesive Ring embodiment of the Hydro-Block Air Vent Condom Catheter
(3) Storage Bag Venting embodiment of the Hydro-Block Air Vent Condom Catheter
(4) Storage Bag Hydro-Block Air Vent
(5) Storage Bag Discharge Tube
(6) Storage Bag
(7) Storage Bag Drain
(8) Storage Bar Drain Cap
(9) Storage Bag Coupler
(10) Inflatable Rings
(11) Hydro-Block Air Vent
(12) Drain Tube Attachment Node
(13) Drain Tube
(14) Hydro-Block Vent Retainer
(15) Hydro-Block Vent Retainer Air Holes
(16) Retro-Fit Assembly Drain Tube Attachment Node
(17) Retro-Fit Assembly Housing
(18) Retro-Fit Assembly Housing Air Holes
(19) Retro-Fit Hydro-Block Filter O-Rings
(20) Retro-Fit Hydro-Block Filter
(21) Retro-Fit Assembly
(22) Retro Fit Embodiment of the Hydro-Block Air Vent Condom Catheter
(23) Condom
(24) Adhesive Strips (25) Drain Tube Coupler
(26) Inflatable Rings Port
(27) Compressed Air Source Valve
(28) Compressed Air Source
(29) Retro-Fit Urine Discharge Channel
(30) Pump and Sensor Connector
(31) Pressure Relief Balloon
(32) Liquid Hose
(33) Sensor Hose
(34) Quick Disconnect with Urine Sensor
(35) Interior Liquid Collection Area
(36) User Selected Pump Means
(37) Liquid Sensor

DETAILED DESCRIPTION OF THE PREFERRED EMBODIMENTS:

1) The Inflatable Ring embodiment of the Hydro-Block Air Vent Condom Catheter.

The Inflatable Ring embodiment of the Hydro-Block Air Vent Condom Catheter (1) depicted in FIG. 1 is manufactured and comprised of the following components in their respective functional relationships:

The Inflatable Ring embodiment of the Hydro-Block Air Vent Condom Catheter (1) is formed in a size and shape capable of fitting over a human penis and forming a fluid tight seal around the penis in general and the glans of the penis in particular. The Inflatable Ring embodiment of the Hydro-Block Air Vent Condom Catheter (1) is comprised of Hydro-Block Air Vent (11) material which permits air to enter into the Inflatable Ring embodiment of the Hydro-Block Air Vent Condom Catheter (1) while simultaneously preventing fluids from escaping therefrom. In the Inflatable Ring embodiment of the Hydro-Block Air Vent Condom Catheter (1) the device is held in place on the shaft of the penis proximally to the glans of the penis by an attachment means comprised of a plurality of Inflatable Rings (10), a Compressed Air Source (28), an Inflatable Rings Port (26) and Compressed Air Source Valve (27). The Inflatable Rings (10) are operatively connected to a Compressed Air Source (28) by means of an Inflatable Rings Port (26). The Compressed Air Source (28) delivers compressed air to the Inflatable Rings (10) through the Inflatable Rings Port (26) inflating thereby and forming a fluid tight seal against the user's penis. The Compressed Air Source (28) can remain attached throughout the use of the device or the user may close the Compressed Air Source Valve (27) thereby permitting the Inflatable Rings (10) to remain in an inflated condition if the user chooses to remove the Compressed Air Source (28) during use of the device. The Inflatable Ring embodiment of the Hydro-Block Air Vent Condom Catheter (1) is further comprised of a Drain Tube Attachment Node (12) which when the device is worn by a user is situated a small distance away from the distal end of the user's penis such that when urine is discharged from the distal end of the urethra urine can easily pass into the Interior Liquid Collection Area (35) and then through the Drain Tube Attachment Node (12) into a the Drain Tube (13) that is removably attached to the Drain Tube Attachment Node (12). Once a user has placed their penis inside the device and it is attached to the user as heretofore described the user may pass urine into the device. During the process of urination gravity and excretion pressure from the user's bladder and urethra will cause the urine to flow through the Drain Tube Attachment Node (12) and into the Drain Tube (13) and away from the user into a user selected collection or disposal means. The urine will not be able to accumulate around the glans or shaft of the penis because the Hydro-Block Air Vent (11) will provide free air flow into the device thereby causing the urine to completely drain away from the penis and ultimately discharge through the Drain Tube (13).

2) Adhesive Ring embodiment of the Hydro-Block Air Vent Condom Catheter.

The Adhesive Ring embodiment of the Hydro-Block Air Vent Condom Catheter (2) depicted in FIG. 2 is manufactured and comprised of the following components in their respective functional relationships:

The Adhesive Ring embodiment of the Hydro-Block Air Vent Condom Catheter (2) is formed in a size and shape capable of fitting over a human penis and forming a fluid tight seal around the penis in general and the glans of the penis in particular. The Adhesive Ring embodiment of the Hydro-Block Air Vent Condom Catheter (2) is comprised of Hydro-Block Air Vent (11) material which permits air to enter into the Adhesive Ring embodiment of the Hydro-Block Air Vent Condom Catheter (2) while simultaneously preventing fluids from escaping therefrom. In the Adhesive Ring embodiment of the Hydro-Block Air Vent Condom Catheter (2) the device is held in place on the shaft of the penis proximally to the glans of the penis by an attachment means comprised of a plurality of Adhesive Strips (24). A user places their penis inside the device and adheres the device to the shaft of the penis proximally to the glans of the penis forming a fluid tight seal against the user's penis. The Adhesive Ring embodiment of the Hydro-Block Air Vent Condom Catheter (2) is further comprised of a Drain Tube Attachment Node (12) which when the device is worn by a user is situated a small distance away from the distal end of the user's penis such that when urine is discharged from the distal end of the urethra urine can easily pass into the Interior Liquid Collection Area (35) and then through the Drain Tube Attachment Node (12) into a the Drain Tube (13) that is removably attached to the Drain Tube Attachment Node (12). Once a user has placed their penis inside the device and it is attached to the user as heretofore described the user may pass urine into the device. During the process of urination gravity and excretion pressure from the user's bladder and urethra will cause the urine to flow through the Drain Tube Attachment Node (12) and into the Drain Tube (13) and away from the user into a user selected collection or disposal means. The urine will not be able to accumulate around the glans or shaft of the penis because the Hydro-Block Air Vent (11) will provide free air flow into the device thereby causing the urine to completely drain away from the penis and ultimately discharge through the Drain Tube (13).

3) Storage Bag Venting embodiment of the Hydro-Block Air Vent Condom Catheter.

The Storage Bag Venting embodiment of the Hydro-Block Air Vent Condom Catheter (3) depicted in FIGS. 3 and 4 is manufactured and comprised of the following components in their respective functional relationships:

The Storage Bag Venting embodiment of the Hydro-Block Air Vent Condom Catheter (3) is formed in a size and shape capable of fitting over a human penis and forming a fluid tight seal around the penis in general and the glans of the penis in particular. The Storage Bag Venting embodiment of the Hydro-Block Air Vent Condom Catheter (3) is comprised of a Condom (23) having a user selected attachment means currently available with existing art condom catheters. In the Storage Bag Venting embodiment of the Hydro-Block Air Vent Condom Catheter (3) the device is held in place by means of the Condom (23) which is placed over the shaft of the penis proximally to the glans of the penis and attached thereto by the user selected attachment means currently available with existing art condom catheters. A user first places their penis inside the Condom (23) and then will adhere the device to the shaft of the penis proximally to the glans of the penis forming a fluid tight seal against the user's penis by the user selected attachment means currently available with existing art condom catheters. The Storage Bag Venting embodiment of the Hydro-Block Air Vent Condom Catheter (3) is further comprised of a Drain Tube Attachment Node (12) which when the device is worn by a user is situated a small distance away from the distal end of the user's penis such that when urine is discharged from the distal end of the urethra urine can easily pass into the Interior Liquid Collection Area (35) and then through the Drain Tube Attachment Node (12) into a the Drain Tube (13) that is removably attached to the Drain Tube Attachment Node (12). The Drain Tube (13) is further comprised of a Drain Tube Coupler (25) at the distal end of the Drain Tube (13) which permits the user to couple with a fluid tight seal the Drain Tube (13) to a Storage Bag Discharge Tube (5) such that when urine is discharged into the Condom (23) by a user the urine may freely pass without leakage through the Drain Tube Attachment Node (12), then into and through the Drain Tube (13), then into and through the Drain Tube Coupler (25), and then into and through the Storage Bag Discharge Tube (5) into a Storage Bag (6) by means of a fluid tight seal. The Storage Bag Discharge Tube (5) is further comprised of a Storage Bag Hydro-Block Air Vent (4). Once a user has placed their penis inside the device and it is attached to the user as heretofore described the user may pass urine into the device. During the process of urination gravity and excretion pressure from the user's bladder and urethra will cause the urine to flow through the Drain Tube Attachment Node (12) and into the Drain Tube (13) and away from the user into a user selected collection or disposal means. The urine will not be able to accumulate around the glans or shaft of the penis because the Storage Bag Hydro-Block Air Vent (4) will provide free air flow into the device thereby causing the urine to completely drain away from the penis and ultimately discharge through into the Storage Bag (6). The Storage Bag (6) in order to be reusable is further comprised of a Storage Bag Drain (8) that is fluid sealable by means of a Storage Bag Drain Cap (9).

4) The Retro Fit Embodiment of the Hydro-Block Air Vent Condom Catheter.

The Retro Fit Embodiment of the Hydro-Block Air Vent Condom Catheter (22) depicted in FIGS. 5, 6, 7 and 8 is manufactured and comprised of the following components in their respective functional relationships:

The Retro Fit Embodiment of the Hydro-Block Air Vent Condom Catheter (22) is generally comprised of three components: a Condom (23) having a user selected attachment means currently available with existing art condom catheters; a Retro-Fit Assembly (21); and a Drain Tube (13). In the Retro Fit Embodiment of the Hydro-Block Air Vent Condom Catheter (22) the device is held in place on the user's penis by means of the Condom (23) which is placed over the shaft of the penis proximally to the glans of the penis and attached thereto by the user selected attachment means currently available with existing art condom catheters. A user first places their penis inside the Condom (23) and then will adhere the device to the shaft of the penis proximally to the glans of the penis forming a fluid tight seal against the user's penis by the user selected attachment means currently available with existing art condom catheters. The Retro-Fit Assembly (21) is further comprised of: a Hydro-Block Vent Retainer (14), a plurality of Hydro-Block Vent Retainer Air Holes (15), a Retro-Fit Assembly Drain Tube Attachment Node (16), a Retro-Fit Assembly Housing (17), a plurality of Retro-Fit Assembly Housing Air Holes (18), at least two Retro-Fit Hydro-Block Filter O-Rings (19), a Retro-Fit Hydro-Block Filter (20) and a Retro-Fit Urine Discharge Channel (29). The Retro-Fit Assembly Housing (17) may be formed from any suitable material such as acetyl copolymer having disposed there through a Retro-Fit Urine Discharge Channel (29) that will permit user discharged urine to pass through and exit the Retro-Fit Assembly Housing (17) through the Retro-Fit Assembly Drain Tube Attachment Node (16) and into the Drain Tube (13) that is removably attached to the Retro-Fit Assembly Drain Tube Attachment Node (16). The Retro-Fit Assembly Housing (17) also has a plurality of Retro-Fit Assembly Housing Air Holes (18) that permit ambient air to freely flow from the outside of the Retro-Fit Assembly Housing (17) to the inside thereof. At least two Retro-Fit Hydro-Block Filter O-Rings (19) are removably attached forming a fluid tight seal between the Retro-Fit Hydro-Block Filter (20) and the Retro-Fit Assembly Housing (17) once the Hydro-Block Vent Retainer (14) is attached to the Retro-Fit Assembly Housing (17) by a snap fit or other suitable attachment means. The Retro-Fit Hydro-Block Filter O-Rings (19) also form a fluid tight seal between the Retro-Fit Urine Discharge Channel (29) and the Retro-Fit Assembly Housing Air Holes (18). The Retro-Fit Assembly Housing (17) is positioned in the distal end of the Condom (23) with the Drain Tube Attachment Node (16) and the Retro-Fit Assembly Housing Air Holes (18) protruding therefrom and exposed to ambient air, but otherwise forming a fluid tight seal with the Condom (23) such that discharged urine will not leak from the device but rather will pass out of the Condom (23) then into the Interior Liquid Collection Area (35) and then through the Retro-Fit Assembly (21) by means of the Retro-Fit Urine Discharge Channel (29) and then into the removably attached Drain Tube (13) and into a user selected collection or disposal means. Once the Retro Fit Embodiment of the Hydro-Block Air Vent Condom Catheter (22) is completely assembled and attached to a user and the user urinates, the expulsion force of urination and/or the force of gravity cause the urine to pass out of the Condom (23) then through the Retro-Fit Assembly (21) by means of the Retro-Fit Urine Discharge Channel (29) and then into the removably attached Drain Tube (13) and into a user selected collection or disposal means. The urine will completely drain by means of venting with ambient air that passes from the environment through the Retro-Fit Assembly Housing Air Holes (18) through a fluid tight channel formed by the Retro-Fit Hydro-Block Filter O-Rings (19) then through the Retro-Fit Hydro-Block Filter (20) and then through the Hydro-Block Vent Retainer Air Holes (15) of the Hydro-Block Vent Retainer (14) and into the Retro-Fit Urine Discharge Channel (29) thereby facilitating the complete drainage by venting of urine without leakage because of the fluid tight ventilation properties of the Retro-Fit Hydro-Block Filter (20).

5) The Modified Retro Fit Embodiment of the Hydro-Block Air Vent Condom Catheter with Quick Disconnect, Pump Connectivity and Automatic Urine Sensing for Pump Activation.

The Retro Fit Embodiment of the Hydro-Block Air Vent Condom Catheter (22) depicted in FIGS. 5, 6, 7 and 8 has been modified as depicted in FIGS. 9 and 10 and wherein the Drain Tube (13) has been substituted with a quick disconnect system with pump connectivity and urine sensing to activate a pump comprised of a Pump and Sensor Connector (30), a Pressure Relief Balloon (31), a Liquid Hose (32), a Sensor Hose (33), and Quick Disconnect with Urine Sensor (34). This modified embodiment is manufactured and comprised of the following components in their respective functional relationships:

The Retro Fit Embodiment of the Hydro-Block Air Vent Condom Catheter (22) as depicted in FIGS. 7 and 8 has been modified as depicted in FIGS. 9 and 10 such that it is generally comprised of: a Condom (23) having a user selected attachment means currently available with existing art condom catheters; a Retro-Fit Assembly (21); a Pump and Sensor Connector (30); a Pressure Relief Balloon (31); a Liquid Hose (32); a Sensor Hose (33); and Quick Disconnect with Urine Sensor (34). In the modified Retro Fit Embodiment of the Hydro-Block Air Vent Condom Catheter (22) of FIGS. 7,8,9, and 10 the device is held in place on the user's penis by means of the Condom (23) which is placed over the shaft of the penis proximally to the glans of the penis and attached thereto by the user selected attachment means currently available with existing art condom catheters. A user first places their penis inside the Condom (23) and then will adhere the device to the shaft of the penis proximally to the glans of the penis forming a fluid tight seal against the user's penis by the user selected attachment means currently available with existing art condom catheters. The Retro-Fit Assembly (21) is further comprised of: a Hydro-Block Vent Retainer (14), a plurality of Hydro-Block Vent Retainer Air Holes (15), a Retro-Fit Assembly Drain Tube Attachment Node (16), a Retro-Fit Assembly Housing (17), a plurality of Retro-Fit Assembly Housing Air Holes (18), at least two Retro-Fit Hydro-Block Filter O-Rings (19), a Retro-Fit Hydro-Block Filter (20) and a Retro-Fit Urine Discharge Channel (29). The Retro-Fit Assembly Housing (17) may be formed from any suitable material such as acetyl copolymer having disposed there through a Retro-Fit Urine Discharge Channel (29) that will permit user discharged urine to pass into the Interior Liquid Collection Area (35) and then through and exit the Retro-Fit Assembly Housing (17) through the Retro-Fit Assembly Drain Tube Attachment Node (16) and into the Liquid Hose (32) that is removably attached to the Retro-Fit Assembly Drain Tube Attachment Node (16) by means of a Quick Disconnect with Urine Sensor (34). The Retro-Fit Assembly Housing (17) also has a plurality of Retro-Fit Assembly Housing Air Holes (18) that permit ambient air to freely flow from the outside of the Retro-Fit Assembly Housing (17) to the inside thereof. At least two Retro-Fit Hydro-Block Filter O-Rings (19) are removably attached forming a fluid tight seal between the Retro-Fit Hydro-Block Filter (20) and the Retro-Fit Assembly Housing (17) once the Hydro-Block Vent Retainer (14) is attached to the Retro-Fit Assembly Housing (17) by a snap fit or other suitable attachment means. The Retro-Fit Hydro-Block Filter O-Rings (19) also form a fluid tight seal between the Retro-Fit Urine Discharge Channel (29) and the Retro-Fit Assembly Housing Air Holes (18). The Retro-Fit Assembly Housing (17) is positioned in the distal end of the Condom (23) with the Drain Tube Attachment Node (16) and the Retro-Fit Assembly Housing Air Holes (18) protruding therefrom and exposed to ambient air, but otherwise forming a fluid tight seal with the Condom (23) such that discharged urine will not leak from the device but rather will pass out of the Condom (23) then through the Retro-Fit Assembly (21) by means of the Retro-Fit Urine Discharge Channel (29) and then into the removably attached Liquid Hose (32) that is removably attached to the Retro-Fit Assembly Drain Tube Attachment Node (16) by means of a Quick Disconnect with Urine Sensor (34) and into a user selected collection or disposal means. Once the modified Retro Fit Embodiment of the Hydro-Block Air Vent Condom Catheter (22) is completely assembled and attached to a user and the user urinates, the expulsion force of urination and/or the force of gravity cause the urine to pass out of the Condom (23) then through the Retro-Fit Assembly (21) by means of the Retro-Fit Urine Discharge Channel (29) and then into the removably attached Liquid Hose (32) that is attached by means of the Quick Disconnect with Urine Sensor (34) which senses the presence of urine and electronically communicates the presence of urine by means of the Pump and Sensor Connector (30) to a User Selected Pump Means (36) (such as the AMXD Max urine disposal pump) with collection or disposal means that is activated thereby and will evacuate the urine from the system and automatically shut off once the Quick Disconnect with Urine Sensor (34) no longer detects the presence of urine. The urine will completely drain by means of venting with ambient air that passes from the environment through the Retro-Fit Assembly Housing Air Holes (18) through a fluid tight channel formed by the Retro-Fit Hydro-Block Filter O-Rings (19) then through the Retro-Fit Hydro-Block Filter (20) and then through the Hydro-Block Vent Retainer Air Holes (15) of the Hydro-Block Vent Retainer (14) and into the Retro-Fit Urine Discharge Channel (29) thereby facilitating the complete drainage by venting of urine without leakage because of the fluid tight ventilation properties of the Retro-Fit Hydro-Block Filter (20). The proper pumping and evacuation of the urine is facilitated by the Pressure Relief Balloon (31) which prevents air and fluid locks in the system that could prevent the proper pumping and/or draining of urine from the system. As depicted in FIG. 10, the sensing of liquid can also be located in the condom by means of a Liquid Sensor (37). All of the fluid sensors of this invention can communicate with a pumping means either directly by conductive wire or by wireless transmission.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. Accordingly, the scope of the invention should be determined not by the embodiments illustrated, but by the claims and their legal equivalents which accompany this application.

Having described my invention, I claim:

1. A Hydro-Block Air Vent Condom Catheter comprised of:
   a condom;
   the condom being comprised of: a proximal opening of a size capable of passing a penis there through; a distal end having an interior liquid collection area; and a distal opening within the distal end of a size capable of permitting a liquid to pass there through;
   the condom being further comprised of an attachment means capable of securing the condom to a user's penis such that urine discharged from the penis would generally enter into the interior liquid collection area and exit the condom through the distal opening;
   a liquid sensor;
   a liquid hose;
   a pressure relief balloon capable of regulating liquids in the liquid hose such that the liquid sensor will detect the presence of liquids without air bubble interference;
   a liquid blocking air vent attached to the condom wherein the liquid blocking air vent permits ambient air to enter into or escape from the condom and prevents liquid from escaping from within the condom; and
   a collection means attached to the distal end of the condom wherein the collection means facilitates the passage of urine from the condom to a user selected disposal means.

2. The Hydro-Block Air Vent Condom Catheter of claim 1 wherein the distal end of the condom is further comprised of:
- a connector positioned between the distal end of the condom and the collection means whereby by means of the connector the collection means may be removed or reattached.

3. The Hydro-Block Air Vent Condom Catheter of claim 1 wherein the collection means is comprised of:
- a condom attachment means;
- a sensor hose;
- a pump and sensor connector wherein the pump and sensor connector is capable of being connected to a user selected pump; and
- the collection means is attached to the condom by the condom attachment means thereby permitting a user's urine to: pass out of the distal end of the condom; be detected by the liquid sensor thereby electronically transmitting data regarding the presence of the user's urine to the pump and sensor connector through the sensor hose thereby facilitating the activation of the user selected pump which when attached and activated draws urine away from the condom exiting the distal end of the condom into the liquid hose, then through the pump and sensor connector and then through the user selected pump to a user selected disposal means.

4. The Hydro-Block Air Vent Condom Catheter of claim 1 wherein the collection means is comprised of:
- a drain tube attached to the distal end of the condom; and
- a storage bag attached to the drain tube wherein urine being discharged by a user will pass out of the distal end of the condom into the drain tube and then pass into the storage bag.

5. The Hydro-Block Air Vent Condom Catheter of claim 4 wherein the drain tube is further comprised of:
- a liquid blocking air vent attached to the drain tube wherein the liquid blocking air vent permits ambient air to enter into or escape from the drain tube and prevents liquid from escaping from within the drain tube.

6. The Hydro-Block Air Vent Condom Catheter of claim 3 wherein the liquid sensor is located in the condom such that it will sense the presence of a user's urine upon urination.

7. A method of using the Hydro-Block Air Vent Condom Catheter of claim 1 consisting of the steps of:
- inserting the user's penis in the proximal opening of the condom;
- attaching the condom to the penis by the attachment means;
- positioning the collection means to facilitate a flow of urine from the penis to the disposal means.

8. A method of using the Hydro-Block Air Vent Condom Catheter of claim 3 consisting of the steps of:
- inserting the user's penis in the proximal opening of the condom;
- attaching the condom to the penis by the attachment means;
- positioning the collection means to facilitate a flow of urine from the penis to the disposal means;
- selecting a pump;
- connecting the pump to the pump and sensor connector;
- turning the pump on such that when the liquid sensor detects the presence of the user's urine the pump will turn on and draw the urine away from the condom through the liquid hose then through the pump to be discharged in the user selected disposal means.

* * * * *